United States Patent [19]

Lewis, II et al.

[11] Patent Number: 5,405,513

[45] Date of Patent: Apr. 11, 1995

[54] METHOD AND APPARATUS FOR AN ELECTROCHEMICAL TEST CELL

[75] Inventors: Arnold L. Lewis, II, Dhahran, Saudi Arabia; Gale B. Farquhar, Houston, Tex.

[73] Assignee: Saudi Arabian Oil Company, Dhahran, Saudi Arabia

[21] Appl. No.: 272,328

[22] Filed: Jul. 8, 1994

[51] Int. Cl.⁶ .......................................... G01N 27/26
[52] U.S. Cl. ................... 204/153.11; 204/404; 436/6; 422/53
[58] Field of Search .............. 204/404, 153.11; 436/6; 422/53

[56] References Cited

U.S. PATENT DOCUMENTS

| | | | |
|---|---|---|---|
| 2,671,336 | 3/1954 | Hulsberg | 73/23 |
| 2,956,225 | 10/1960 | Marsh et al. | 324/71 |
| 3,042,863 | 7/1962 | Marsh et al. | 324/71 |
| 3,394,080 | 7/1968 | Hoffman et al. | 210/59 |
| 3,531,252 | 9/1970 | Rivers | 23/230 |
| 3,592,212 | 7/1971 | Schleimer | 137/93 |
| 3,866,460 | 2/1975 | Pearce, Jr. | 73/19 |
| 3,942,546 | 3/1976 | Radd et al. | 137/93 |
| 4,033,871 | 7/1977 | Wall | 210/96 R |
| 4,058,373 | 11/1977 | Kurz et al. | 55/16 |
| 4,065,373 | 12/1977 | Martin et al. | 204/404 |
| 4,133,734 | 1/1979 | Polak et al. | 204/404 |
| 4,221,651 | 9/1980 | Mansfeld et al. | 204/404 |
| 4,550,590 | 11/1985 | Kesson | 73/19 |
| 5,062,292 | 11/1991 | Kanba et al. | 73/19.01 |

OTHER PUBLICATIONS k. Suzuki, T. Kouno, E. Sato and T. Murata, "The Study of Inhibitors for Sour Gas Service", *Corrosion*, vol. 38, No. 7, Jul. 1982.

H. Okada, K. Suzuki and J. Kawasaki, "Control of Corrosion and Related Hydrogen Entry into Steel Products by Inhibitors in Sour Gas Environments", Society of Petroleum Engineers, SPE paper No. 6810, pp. 1495-1509, Sep. 6-11, 1981.

C. Christensen and C. Juhl, "Evaluation of Inhibitors for Sour Crude Oil Transmission Lines", *Corrion 88*, St. Louis, Missouri, Mar. 21-25, 1988, NACE Paper No. 198, pp. 198/1198/20.

D. R. Fincher and A. C. Nestle, "New Developments in Monitering Corrosion Control", Materials Performance, vol. 12, No. 7, Jul. 1973. p. 17.

R. M. Vennett, "Corrosion Monitering in Oilfield Operations using a Vacuum Hydrogen Probe", Materials Performance, vol. 16, No. 8. Aug. 1977, p. 31.

S. B. Lyon and D. J. Fray, "Detection of hydrogen generated by corrosion reactions using a solid electrolyte probe", Materials Performance, vol. 23, No. 4, Apr. 1984, p. 23.

H. Arup, "Amperometric Hydrogen Determination with the Sealed Devanathan Cell", Proceedings of International Workshop of Electrochemical Corrosion Testing, Ferrara, Italy, Sep. 11-13. 1985.

*Primary Examiner*—John Niebling
*Assistant Examiner*—Bruce F. Bell
*Attorney, Agent, or Firm*—Davis Hoxie Faithfull & Hapgood

[57] ABSTRACT

A method and apparatus is provided for the simultaneous measurement of the general corrosion rate and the atomic hydrogen permeation rate through at least two like specimens in the same test cell, under the same conditions at the same time.

The nonconductive electrochemical test cell is adapted to receive at least two test specimens and associated electrodes and electronic and physical measuring means. One or more chemical additives can be introduced into the cell to determine their effect on inhibiting hydrogen permeation and corrosion rates as reflected by the respective measurements. This procedure can be repeated for other inhibitors, and, from the data obtained, a comparative ranking of the effectiveness of inhibitors can be assigned.

34 Claims, 2 Drawing Sheets

METHOD AND APPARATUS FOR AN ELECTROCHEMICAL TEST CELL

FIELD OF INVENTION

The present invention relates to a laboratory test method and apparatus for the evaluation of corrosion inhibitors. The invention is particularly useful in comparing the relative effectiveness of two or more chemical inhibitors. The crude oil production industry uses such inhibitors as additives in fluid streams to prolong the service life of pipelines, fittings, valves and vessels exposed to the corrosive and otherwise detrimental effects of sour gas. The invention provides a method and apparatus for the simultaneous measurement of hydrogen permeation rate and general corrosion rate.

BACKGROUND OF THE INVENTION

Crude oil flows through thousands of miles of pipelines worldwide. Such pipelines are typically made of mild steel. Due to the nature of the chemical environment to which the pipeline is exposed, i.e., petroleum, brine and dissolved impurities, the pipeline can be susceptible to two forms of corrosive attack as described below.

First, mild steel pipe is susceptible to general corrosion. Corrosion involves two basic chemical processes—oxidation and reduction. With corrosion of mild steel, the oxidative reaction [1] results in the destruction of the metal matrix.

$$Fe° \rightarrow Fe^{+2} + 2e^- \quad [1]$$

In certain chemical environments, the concurrent reduction reaction results in the formation of atomic hydrogen [2].

$$H^+ + e^- \rightarrow H° \quad [2]$$

In most chemical environments, the atomic hydrogen produced quickly undergoes reaction to form molecular hydrogen [3] which passes harmlessly into the process environment.

$$2H° \rightarrow H_{2(gas)} \quad [3]$$

In those cases of typical corrosion, the formation of molecular hydrogen occurs virtually concurrently with the reduction of hydrogen ion to atomic hydrogen. However, there are several chemical environments in which the combination reaction of atomic hydrogen to form molecular hydrogen is impeded, resulting in a higher concentration, or lifetime, of individual hydrogen atoms at or near the vicinity of the steel surface. One such environment, common to the oil industry, is where hydrogen sulfide gas is present in process fluids. Having atomic hydrogen in close proximity to the surface of mild steel pipe can result in a second form of corrosive attack known as hydrogen induced cracking (HIC).

Atomic hydrogen is very soluble in materials such as the mild steel used to fabricate pipe and process vessels due to the very small size of the hydrogen atom. Atomic hydrogen will therefore quickly diffuse, permeate or migrate into solid steel structures. Hydrogen atoms which permeate completely through a steel structure typically combine to form molecular hydrogen which disperses into the external environment. This phenomena does not deleteriously affect the steel. In contrast, HIC susceptible steel contains voids or inclusions into which atomic hydrogen also diffuses. Once inside an inclusion, atomic hydrogen atoms can combine to form molecular hydrogen which cannot diffuse further into the steel matrix. This molecular hydrogen is trapped in the steel, causing the internal pressure in the void to increase as the number of trapped hydrogen molecules increase. At some point, the pressure in the void reaches a level that is high enough to cause propagation of one or more cracks. Such cracking can eventually lead to a total failure of the pipe.

To counteract the potential damage of HIC, various control methodologies are used in the industry. Certain steel alloys and steel manufacturing processes have been developed which are immune to HIC. However, these HIC-resistant alloys are quite expensive and their use can be economically justified in limited situations. A second control methodology is removal from the process stream of the compound or compounds which impede the formation of molecular hydrogen, which in the case of petroleum feeds is hydrogen sulfide gas. Hydrogen sulfide removal, known as "sweetening," is well known in the oil industry and used in many locations, but it is not always a cost effective choice. A third HIC control method is the addition of chemical inhibitors to the process stream at very low concentration levels.

HIC inhibitors are bi-functional in that they work (1) by lowering the general corrosion rate caused by various feedstock components; and (2) by reducing or eliminating the number of free hydrogen atoms that can migrate into the interior of the walls of the steel pipe. There are a large number of commercially available HIC inhibitors, the effectiveness of which vary with the specific chemical composition of the process stream. Selection of an appropriate inhibitor is further complicated by the fact that an inhibitor may be effective at reducing hydrogen permeation, while at the same time have a poor ability to inhibit general corrosion. Thus, each additive must be tested under process conditions to determine its effectiveness as a general corrosion inhibitor and a hydrogen permeation inhibitor.

Various test methods have been developed for independently testing corrosion and HIC inhibitors. A widely used procedure for corrosion inhibitor evaluation utilizes a "wheel oven." A wheel oven consists of a wheel rotating at a fixed RPM for a given time period in a temperature controlled oven. A number of small sealed bottles are attached to the wheel. The bottles contain a fixed concentration of inhibitor in the aqueous environment to be tested, as well as a preweighed test sample. At the end of the test period the test samples are removed, cleaned and weighed. A general corrosion rate is calculated from sample weight loss and sample area. A ranking of inhibitor performance can be prepared. There are a number of limitations associated with such wheel oven measurements. In particular, since the same solution and gases are present in the bottle throughout the test, the test simulates only a static system and the build up of corrosion products can change solution chemistry. Further, only the general corrosion rate can be determined, not pitting rate, nor can mechanistic corrosion processes or surface effects be determined.

In order to address some of the limitations of the wheel oven, more sophisticated electrochemical methods for corrosion rate measurement were developed. A few of these methods are listed below. In one such method, very small spontaneous current spikes associated with metal oxidation are measured. The data is collected and analyzed by software to develop corrosion rate information. While this procedure is noninvasive to the sample, it requires sophisticated software and data collection instrumentation. In another method, which may be referred to as a polarization resistance method, a small anodic and cathodic potential, typically ±10 millivolts (mv), is applied to the corroding metal substrate and the resulting current is measured. These values are then used to calculate a general corrosion rate. In a third method, a relatively large cathodic and anodic potential, typically 2–300 mv, is applied to the corroding metal substrate and a current is measured. Through data analysis a general corrosion rate is determined, as well as a semiquantitative calculation of pitting rate. This method is damaging to the inhibitor/metal surface film so that typically only one measurement may be taken per 24 hour period. The corrosion rate may be also be determined by electrochemical impedance spectroscopy. In this method, a small amplitude sine wave signal, maximum 5 mv, of varying frequency, typically $10^{-5}$ to $10^5$ Hertz, is applied to the corroding metal. Through analysis of the applied potential, resulting current and phase angle, mechanistic information as to the corrosive phenomena occurring may be obtained.

In contrast to corrosion rate testing, which is widely practiced using many different methods, inhibitors are not routinely evaluated as to their effectiveness as atomic hydrogen permeation mitigators. Further, there are a limited number of methods available for monitoring hydrogen permeation. In a first method, the permeation of corrosion generated hydrogen into a steel container of fixed volume is monitored by determining the increase in pressure within the container. In a second method, HIC mitigation is evaluated as a function of hydrogen permeation current density, which is the measured variable. Both of these methods are utilized in conjunction with the present invention.

While a number of methods exist for determining the general corrosion rate, and at least two methods exist for the evaluation of hydrogen permeation inhibition effectiveness, the prior art methods do not allow simultaneous measurement of an inhibitor's ability to inhibit hydrogen permeation and general corrosion. Using the teachings of the prior art, such measurements are carried out in different test cells. The results obtained from the same test cell are known to be reliable to only about ±25% due to factors such as variation in stir rate and gas flow rate, temperature fluctuations, the difficulty in pipetting small volumes of very viscous corrosion inhibitors, cell cleanliness, and variation in the brine makeup and in the ratio of solution volume to sample surface area. Thus, where corrosion inhibition and hydrogen permeation inhibition are not tested in the same cell simultaneously, variation in cell conditions hampers reliable evaluation of HIC inhibitor overall performance.

The above discussion of HIC and the use of corrosion inhibitors to control it, pertains to carbon steels having yield strengths less than about 90,000 psi. In the case of higher strength steels having a yield strength above 90,000 psi, the nature of the stress cracking and failure is different. Unlike the more gradual blistering and cracking which ultimately leads to fracture failure in the former class of steels, an instantaneous, catastrophic failure occurs in high strength steels. This is known as sulfide stress cracking (SSC). Due to the instantaneous nature of SSC failures, the use of corrosion inhibition additives to the fluid stream is not considered a viable control method. When SSC problems are anticipated, they are typically addressed metallurgically.

It is therefore an object of this invention to provide a more reliable means for evaluating HIC inhibitor performance.

It is a further object of this invention to provide an improved means for selecting an HIC inhibitor.

SUMMARY OF THE INVENTION

The aforementioned problems are solved and a technical advance in the art is achieved by a method and apparatus in which the general corrosion rate and the atomic hydrogen permeation rate are measured in the same test cell at the same time.

An electrochemical test cell made of nonconductive material is physically adapted to receive two test samples; one, a corrosion test sample, the other, a hydrogen permeation test sample. The samples are simultaneously exposed to the same process environment in the test cell. Hydrogen sulfide is introduced into the test cell to impede the formation of molecular hydrogen.

In a first embodiment, a hydroxide reservoir containing sodium hydroxide is secured to the exterior of the cell body and in fluid communication with the permeation test sample. Hydrogen atoms which have permeated the test sample are oxidized to hydrogen ions by the electrochemical conditions present in the cell. The sodium hydroxide in the reservoir then neutralizes the hydrogen ions. The hydrogen permeation rate is determined from the current produced from the electrochemical oxidation of hydrogen.

In a second embodiment, the hydrogen passing through the permeation test sample is collected in the presence of a pressure transducer located in a chamber secured to the exterior wall of the cell body. The hydrogen permeation rate is determined based on the rate of pressure increase.

The corrosion rate, which is based on data taken from the corrosion test sample and associated electrodes, is determined by standard methods. Measurements are taken before and after the addition of HIC/corrosion inhibitors to the process fluid.

Inhibitor effectiveness is measured as a function of the ratio of the permeation current density to the corrosion current density. As between competing HIC inhibitors, the inhibitor associated with the lowest value of the calculated ratios is deemed to be relatively more effective.

In a preferred embodiment, the invention relates to a method for determining the permeation efficiency of a hydrogen induced cracking inhibitor in the presence of at least one compound which impedes the reaction of atomic hydrogen to molecular hydrogen, where permeation efficiency is a function of atomic hydrogen permeation current density and corrosion current density, comprising:

providing a reservoir of corrosive process solution;

simultaneously exposing a first electrically isolated test specimen and a first electrode, and a second electrically isolated test specimen and a second electrode to the process solution;

adding a first compound to said process solution reservoir to impede the reaction by which atomic hydrogen is converted to molecular hydrogen;

measuring the atomic hydrogen permeation current density of the first electrically isolated test specimen and the corrosion current density of the second electrically isolated test specimen in the presence of the first compound;

adding a second compound which inhibits hydrogen induced cracking;

measuring the atomic hydrogen permeation current density of the first electrically isolated test specimen and the corrosion current density of the second electrically isolated test specimen in the presence of the first and second compounds; and determining the permeation efficiency of the second compound, where permeation efficiency is defined as the ratio of the atomic hydrogen permeation current density to the corrosion current density.

These and other objects, features and advantages of the invention will be better understood from consideration of the following detailed description taken in conjunction with the accompanying drawings.

DETAILED DESCRIPTION

Figure 1:
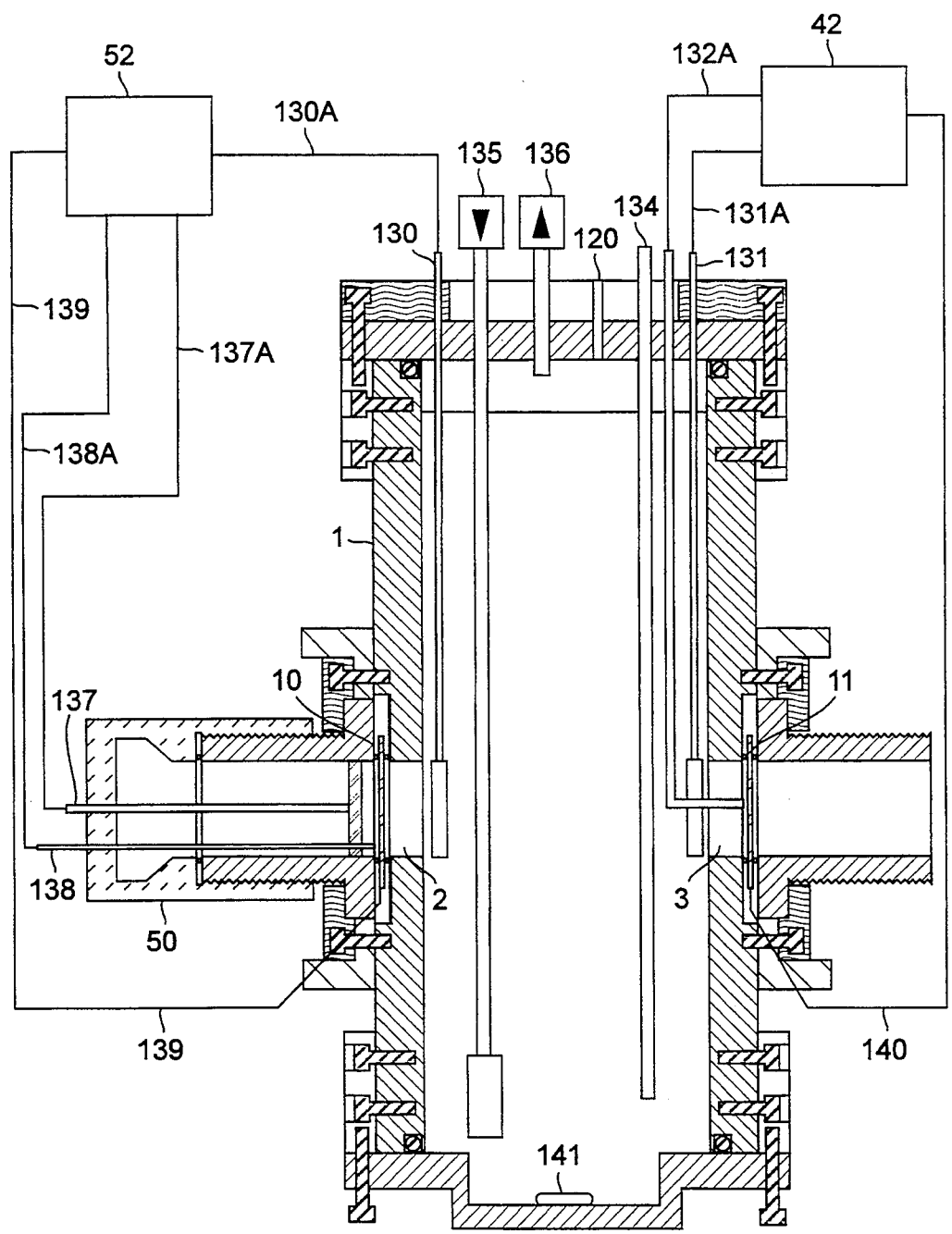
FIG. 1 is a cross-sectional side view of a first embodiment of an electrochemical test cell according to the present invention.

FIG. 1 is a cross-sectional view of an HIC inhibitor evaluation cell according to the present invention. A cell body 1 provides a reservoir for the process fluid. Two sample ports, 2 and 3, are formed in the cell body to receive at least one hydrogen permeation test specimen 10 and one corrosion test specimen 11. The cell body 1 can be made of any material that is inert to the process chemistries for which the cell is used, that is electrically nonconducting and preferably nonadsorptive. Tetrafluoroethylene (sold under the trademark Teflon ®) is presently the preferred material for the cell body. Other materials, including, but not limited to chlorotrifluoroethylene resins (sold under the trademark Kel-F ®), polyvinyldifluoride (sold under the trademark Kynar ®), polyetheretherketone (PEEK) and machinable ceramic can also be used, but they are more expensive than Teflon ®.

As noted above, the cell body 1 should be made of a nonconductive material. This facilitates electrical isolation of the test samples. Such electrical isolation of the test samples is critical to the proper functioning of the present invention.

Sample ports 2 and 3 are preferably diametrically opposed to each other, and on the same horizontal plane, on the sides of the cell body 1. By placing the sample ports on opposite sides of the cell body 1, electrical solution resistance between the test specimens 10 and 11, which are placed in sample ports 2 and 3, is maximized. Placement of the sample ports on the same horizontal plane insures that the specimens 10 and 11 are in as similar a chemical environment, in terms of stirring and gas flows, as is possible.

The size of the sample ports 2 and 3 is a function of specimen size. It is desirable to maximize the surface area of the specimen exposed to the cell environment, since one of the measured variables, i.e, permeation current, is directly proportional to the exposed surface area of the specimen. Thus, a large port size is indicated. However, it is important that the ratio of solution volume to test specimen surface area is at least about 50 milliliters per square centimeter ($mL/cm^2$) and preferably about 100 $mL/cm^2$. If this ratio decreases below about 50 $mL/cm^2$, solution chemistry may be altered as a result of the accumulation of corrosion products. Thus, the desire for a larger specimen/sample port must be balanced by the requirement of a larger test cell. Two inch (in.) diameter test specimens represent a suitable compromise between test cell size and the magnitude of the permeation current. The diameter of sample ports 2 and 3 is 1.35 in., which was selected, in conjunction with the specimen size, to accept a standard o-ring seal. The o-ring seal, or equivalent, is required to seal the sample specimen to the cell body. The particular size of the o-ring should maximize test specimen exposure to the process fluid. A suitable o-ring is number ARP 568-127.

The hydrogen permeation test specimen 10 and corrosion test specimen 11 are machined as circular solid disks. Test specimens should have the same thickness, since the permeation current peaks are affected by the thickness of the specimen. A suitable thickness for the test specimens 10 and 11 is 0.03 in. Since the corrosion rate and the hydrogen permeation rate appear to be affected by specimen surface characteristics, each sample should have a uniform, identifiable finish. A relatively smooth finish, such a 320 grit, is suitable. The surfaces should be degreased with, for example, n-hexane, and rinsed with deionized water prior to use.

The test specimens 10 and 11 are made from the same type or grade of mild steel used in the pipelines in which the inhibitors will be used. The test specimen can, for example, be taken from HIC resistant mild steel pipe, such as A106 seamless mild steel pipe. About 10% of both surfaces of the pipe should be machined away to insure that the specimen is completely HIC resistant. Samples must be free of any internal voids or occlusions that can result in lost atomic hydrogen which would reduce signal levels and precision. In addition, one side of test specimen 10 is preferably plated with elemental palladium to a minimum thickness of 0.00005 inches. The palladium coating, although not required, insures that the surface is inert and will not oxidize under the electrochemical steps that are performed to measure the atomic hydrogen permeation rate. In addition, a palladium coating provides a five-fold increase in the signal-to-background ratio over uncoated surfaces.

Electrically conductive means 139, 140 suitable for transmission of a signal, preferably 22-gauge wire, are attached to the outer edge of each test specimen 10, 11, respectively, for electrical connection to suitable electronic measurement means.

Test specimens 10 and 11 are secured in the sample ports in a manner which provide a fluid-tight seal. Hydrogen collection device or means 50, 60 is placed in sealing relation with the surface of permeation test specimen 10 opposite the surface that is in contact with the process fluid, i.e., on the exterior of the cell wall.

In a first preferred embodiment illustrated in FIG. 1, the hydrogen collection device is a hydroxide reservoir 50. The hydroxide reservoir is adapted to receive a permeation counter electrode 137 and permeation reference electrode 138. The permeation reference electrode 138 is positioned as close as practical to the palladium surface of permeation test specimen 10. The permeation counter electrode 137 is made of a material inert to the chemical environment. In view of the harsh environment of the hydroxide reservoir, the permeation counter electrode 137 is preferably made of platinum. Such an electrode is available from Johnson-Matthey. The permeation reference electrode 138 may be formed by sealing a platinum wire in a length of Pyrex ® glass tubing.

The hydroxide reservoir 50 is further provided with resealable openings or ports so that the reservoir can be filled with a strong base such as sodium or potassium hydroxide solution. The hydroxide solution should have a pH of at least 13.

Hydrogen atoms that have permeated the permeation test specimen 10 are oxidized to hydrogen ion by the cell electrochemistry. Such hydrogen ions react readily with the hydroxide ions present in the hydroxide reservoir to form water. Neutralizing the hydrogen ion in this manner maintains the pH of the hydroxide solution in the hydroxide reservoir 50. A change in pH would alter the solution chemistry thereby interfering with the hydrogen permeation measurements. Further, a pH of at least 13 prevents oxidation of the permeation test specimen 10. As mentioned previously, the palladium coating applied to the surface of the specimen 10 in communication with the hydroxide reservoir 50 also aids in preventing oxidation of the specimen 10.

Figure 2:
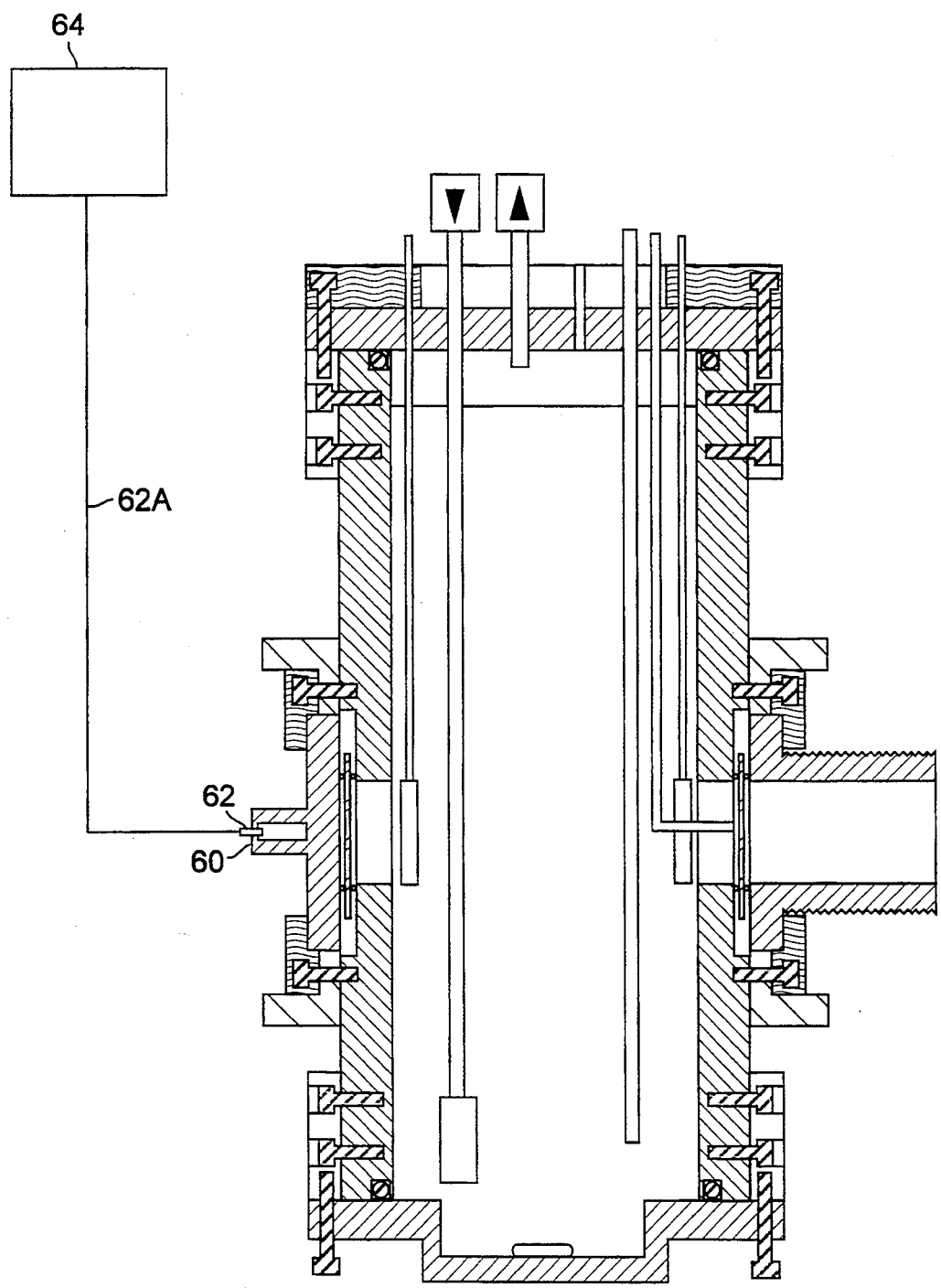
FIG. 2 is a side cross-sectional side view of a second embodiment of an electrochemical test cell according to the present invention.

In a second preferred embodiment of FIG. 2, the hydrogen collection means or device is a pressure chamber 60, which is adapted to receive fluid pressure measurement means 62, such as a high accuracy pressure transducer. The pressure measurement device 62 is connected to suitable electronic measurement means 64 known in the art. Pressure in the chamber 60 increases due to the passage of hydrogen through the permeation test specimen 10. Measurement means 62 produces a signal indicative of the increase in pressure that is transmitted to the electronic measurement means 64 via a conductor 62A, or other means suitable for transmission of a signal. The hydrogen permeation rate is determined based on the rate of pressure increase.

As shown in FIG. 1, the HIC inhibitor cell is adapted to receive various measurement devices. Counter electrodes 130 and 131, preferably of stainless steel, are positioned in the cell body directly in front of each sample port. The counter electrode located at sample port 2 housing the hydrogen permeation test specimen 10 is referred to as the permeation charging counter electrode 130. The counter electrode located at sample port 3 housing the corrosion test specimen 11 is referred to as the corrosion counter electrode 131. The corrosion reference electrode 132 is positioned as close as practical to the corrosion test specimen 11. The corrosion reference electrode 132 may be a saturated calomel electrode used in conjunction with a salt bridge, a stainless steel wire embedded in a glass tube, or have other configurations known to those skilled in the art. A probe 134 is used for temperature measurement, and gas inlet 135 and outlet 136 with appropriate values are positioned in the test cell.

A small port 120 is located on top of the test cell 1. This port, known as a septum port, is adapted to receive a syringe or like means, by which the inhibitor to be tested can be injected into the reservoir of test cell 1.

The permeation counter electrode 137, permeation reference electrode 138, permeation charging counter electrode 130 and permeation test sample 10 are connected, respectively, by electrical conductors 137A, 138A and 139, or other means suitable for transmission of a signal, to electronic hydrogen permeation measurement means 52 which is provided with functions for applying a potential to the respective electrodes, measurement, monitoring, display, recording and/or analysis of hydrogen permeation data. Devices suitable for performing such functions, such as potentiostats, are well known in the art.

The corrosion counter electrode 131, corrosion reference electrode 132 and corrosion test sample 11 are connected, respectively, by electrical conductors 131A, 132A and 140, or other means suitable for transmission of a signal, to electronic corrosion measurement means 42 which is provided with functions for applying a potential to the respective electrodes, measurement, monitoring, display, recording and/or analysis of corrosion data. Devices suitable for performing such functions are also well known in the art.

Conductive wiring is used to connect the test specimens 10, 11 to the measurement electronics 42, 52. It is important that the wiring not be exposed to either the hydroxide solution or the test cell solution in order to maintain electrical isolation of the specimens and prevent galvanic couples.

The functioning of the aforementioned electrodes, test specimens and measurement means is explained below.

In a preferred embodiment, the well known polarization resistance method is used for measuring corrosion rate. In this method, the electronic corrosion measurement means 42 sequentially applies different voltage potentials to the counter electrode 131 to achieve several desired potentials at the working electrode, i.e., corrosion test specimen 11. For example, potentials of +0.010, 0.0 and −0.010 volts vs. ground are established at test specimen 11. The current flowing between the corrosion counter electrode 131 and the corrosion test specimen 11 is measured at each of these potentials. A corrosion rate may then be calculated using a well known algorithm. The corrosion reference electrode 132 functions as a feedback element to ensure that the desired potential is applied to the corrosion test specimen 11.

Simultaneously, in the hydroxide reservoir, the electronic permeation measurement means 52 applies a voltage potential to the permeation counter electrode 137 so that a desired potential results at the working electrode, i.e., the permeation test specimen 10. The permeation reference electrode 138, like permeation counter electrode 137, ensures the desired potential is applied to the permeation test specimen 10. In a preferred embodiment, the potential at the test specimen 10 is maintained at −0.125 volts with respect to analog ground and the permeation reference electrode 138. This potential has been found to be large enough to instantly oxidize any atoms of hydrogen that permeate the test specimen 10 into the hydroxide reservoir 50, yet not cause oxidation of the test specimen 10. Oxidation of the atomic hydrogen which has passed through the test specimen 10 produces a current, the hydrogen permeation current, which is measured by the electronic permeation measurement means 52.

The charging counter electrode 130 can be used to apply a charging current, typically 50 to 150 milliamps per $cm^2$ of exposed test specimen surface area, to the surface of the permeation test specimen 10. This current is not required to obtain the hydrogen permeation rate and general corrosion rate of a specimen. In certain cases, however, application of the charging current may simulate the longer exposure times to corrosive environments experienced in the field thus improving the applicability of the test cell data. The charging counter electrode 130 is connected by conductor 130A, or other suitable means, to electronic hydrogen permeation measurement means 52.

In operation, the cell body is filled with process solution, typically a high salinity brine. Suitable solutions include NACE TM-0177-86 and NACE TM-0284-87. The TM-0177-86 solution is 94.5 percent by weight deionized or distilled water, 0.5 percent glacial acetic acid and 5.0 percent sodium chloride. The TM-0284-87 solution is prepared in accordance with ASTM STANDARD SPECIFICATION D 1141, stock solutions 1 and 2, without heavy metal ions.

The stirrer 141 is activated and maintained at a stir rate of approximately 300 to 400 rpm. Cell temperature is monitored and maintained at approximately 25° C., which is the standard temperature for such measurements. A heating/cooling jacket or other means for controlling temperature can be used as required to maintain the cell temperature at 25° C. The head space remaining in the cell is purged with nitrogen gas to eliminate oxygen. The hydroxide reservoir is filled with 0.1N sodium or potassium hydroxide solution.

When the background current of the permeation test specimen is stable, e.g., at less than about 1 microamp per square centimeter, the nitrogen gas flow is stopped and hydrogen sulfide gas flow is started. For a cell with a two liter process solution capacity, a hydrogen sulfide gas flow of about ten milliliters per minute is adequate. The atomic hydrogen permeation rate and corrosion rate measurements are obtained and recorded. Thereafter, a known volume of an inhibitor to be tested is injected into the cell through the septum port 120 using a syringe. The atomic hydrogen permeation rate and corrosion rate measurements are again obtained and recorded. Comparable data for any number of different inhibitors can be obtained in this manner. Data acquisition and analysis are preferably computerized and automated through the use of a suitably programmed general purpose computer.

The following illustrative example shows the advantage of the present invention in measuring hydrogen permeation and corrosion rates simultaneously in a single cell.

EXAMPLE

Improved Reliability Where Permeation Rate and Corrosion Rate are Measured In the Same Test Cell The following example illustrates the use of the present invention for evaluating HIC inhibitors to obtain more reliable and accurate results than can be obtained using prior art methods and apparatus.

The amount of atomic hydrogen that enters a metal surface is characterized by $\alpha$, the permeation efficiency, which is the ratio of the hydrogen permeation current density to the corrosion current density. These current densities are a measure of the rate at which these phenomena occur. Permeation efficiency is a reliable and accurate indication of inhibitor performance.

To calculate $\alpha$ for an HIC inhibitor according to prior art methods, the corrosion current and the hydrogen permeation current must be determined independently of each other by successive test runs in a single test cell, or runs in two different test cells. The procedure is then repeated to evaluate a second HIC inhibitor. To calculate $\alpha$ for an HIC inhibitor according to the present invention requires only a single test run in any given test cell. As previously noted, there is an experimental variability of about 25 percent from run to run in a test cell. Since prior art methods require two test runs to evaluate a single inhibitor, the calculation of $\alpha$ for a given inhibitor is subject to greater variability than when $\alpha$ is determined according to the present invention. Thus, inhibitors can be more reliably evaluated according to the present invention.

The foregoing can be illustrated with hypothetical test cell results based on the following assumptions. First, the chemical changes taking place in the cell results in a hydrogen permeation current density $I_p$ of 40.0 microamperes per square centimeter ($\mu$amps/cm$^2$) and, second, the corrosion rate results in a corrosion current density $I_{corr}$ of 66 $\mu$amps/cm$^2$. As previously noted, the experimental variability is 25 percent.

Thus, the variability of the results in an HIC inhibitor test cell according to the present invention are as follows. $I_p$ ranges from an $I_{p\text{-}minimum}$ of 30 $\mu$amps/cm$^2$ to an $I_{p\text{-}maximum}$ of 50 $\mu$amps/cm$^2$. $I_{corr}$ ranges in value from an $I_{corr\text{-}minimum}$ of 49.5 $\mu$amps/cm$^2$ to an $I_{corr\text{-}maximum}$ of 82.5 $\mu$amps/cm$^2$. Generally, when the corrosion current is at its minimum, the permeation current will also be at a minimum. The same behavior is observed at the maximum. Thus, permeation efficiency $\alpha$ for a given inhibitor will range from a minimum of 0.46 (30.0/66) to a maximum of 0.76 (50/66). In other words, if a test run was performed according to the present invention on an HIC inhibitor characterized as above, the measured value for $\alpha$ is expected to range from 0.46 to 0.76 when its "true" $\alpha$ is 0.61 (0.40/0.66).

The variability of results for HIC inhibitor testing using separate test cells according to the prior art is estimated as follows. The range for $I_p$ and $I_{corr}$ are the same as for the previous case. However, since the hydrogen permeation test and the corrosion test are performed in separate test cells, the respective maxima and minima values cannot be grouped together. The permeation current could be at its minimum value, and the corrosion current, measured separately, could be at its maximum due to variation in cell conditions, resulting in a broader range for $\alpha$. Thus, e will range from a minimum of 0.36 (30/82.5) to a maximum of 1.01 (50/49.5). The range expected for $\alpha$ when the testing is performed according to the present invention is narrower and closer to the "true" value of 0.61 than the range expected when the measurements are performed individually in separate test cells.

We claim:

1. An electrochemical test cell apparatus adapted to simultaneously measure the rate of atomic hydrogen permeation through a first test specimen and the general corrosion rate of a second test specimen resulting from exposure to a corrosive fluid, the test cell apparatus comprising:

a test cell body defining a fluid reservoir fabricated from materials having high electrical resistance;

the cell body having at least first and second sample ports, where said first sample port receives the first test specimen and said second sample port receives the second test specimen, the test specimens are electrically isolated from each other;

the cell body further receive electrodes positioned in the test cell;

an electronic hydrogen permeation measurement device for measuring hydrogen which permeates said first test specimen;

an electronic corrosion measurement device for measuring the corrosion rate of said second test specimen; and means for connecting the electrodes to the hydrogen permeation and corrosion measurement devices.

2. The electrochemical test cell of claim 1 where the cell body is tetrafluoroethylene.

3. The electrochemical test cell of claim 1 further comprising a stirrer.

4. The electrochemical test cell of claim 1 further comprising means for introducing additional materials into the fluid reservoir of the test cell while the test cell is in operation.

5. The electrochemical test cell of claim 4 where the test cell receives liquids and gases.

6. The electrochemical test cell of claim 1 where the reservoir is filled with a corrosive fluid.

7. The electrochemical test cell of claim 6 where the corrosive fluid is brine and hydrogen sulfide.

8. The electrochemical test cell of claim 6 further comprising means for introducing into said test cell compounds which inhibit hydrogen through the first test specimen.

9. A test cell apparatus comprising:
a cell body defining a fluid reservoir, the cell body having
first and second sample ports, the first sample port receives a first test specimen and the second sample port receives a second test specimen;
means for securing the test specimens in fluid-tight relation to said first and second sample ports;
a hydrogen collection device secured to the exterior of the cell reservoir and enclosing the first sample port for collecting hydrogen which permeates the first test specimen;
a device for measuring the amount of hydrogen which permeates the first test specimen into the collection device; and
an electronic corrosion measurement device which applies a voltage potential between a first electrode located in the reservoir and the second test specimen, and to measure the current flow between the first electrode and the second test specimen.

10. The test cell apparatus of claim 9 further comprising a second electrode positioned in the fluid reservoir which functions as a feedback element to maintain a chosen voltage potential at the second test specimen.

11. The test cell of claim 9 where the hydrogen collection device is a hydroxide reservoir containing a solution selected from the group consisting of sodium hydroxide and potassium hydroxide.

12. The test cell of claim 11 where the pH of the hydroxide solution is at least 13.

13. The test cell of claim 11 where the device for measuring the amount of hydrogen which permeates the first test specimen comprises an electronic hydrogen permeation measurement device for applying a voltage potential between a primary electrode in the hydroxide reservoir and the first test specimen, and for measuring the current flow between the primary electrode in the hydroxide reservoir and the first test specimen.

14. The test cell of claim 13 which further comprises a second electrode which functions as a feedback element to maintain a chosen potential at the first test specimen.

15. The test cell of claim 9 where the hydrogen collection device is a pressure chamber.

16. The test cell of claim 15 where the device for measuring the amount of hydrogen permeating the first test specimen comprises a pressure transducer and an electronic measurement device.

17. The test cell of claim 9 where the cell body is a nonconductive material.

18. The test cell of claim 9 where the cell body is tetrafluoroethylene.

19. A method for the simultaneous determination of atomic hydrogen permeation rate and general corrosion rate of metals comprising:
providing a corrosive process solution in a test cell;
simultaneously exposing a first electrically isolated test specimen and a first electrode, and a second electrically isolated test specimen and a second electrode to the process solution in the same test cell; and
simultaneously measuring the atomic hydrogen permeation rate through the first electrically isolated test specimen and the corrosion rate of the second electrically isolated test specimen.

20. The method of claim 19 where the process solution is a brine solution.

21. The method of claim 20 which includes the steps of adding to the process solution a compound to impede the reaction of atomic hydrogen to molecular hydrogen, and then simultaneously measuring the atomic hydrogen permeation rate through the first electrically isolated test specimen and the corrosion rate of the second electrically isolated test specimen.

22. The method of claim 20 where the process solution comprises hydrogen sulfide.

23. The method of claim 19 where the step of simultaneously measuring the atomic hydrogen permeation rate through the first electrically isolated test specimen and the corrosion rate of the second electrically isolated test specimen comprises:
(a) applying a first voltage potential to the second electrode and to the second electrically isolated test specimen;
(b) measuring the current flowing between the second electrode and the second electrically isolated test specimen at the first potential;
(c) simultaneously applying a voltage potential to the first electrode and the first electrically isolated test specimen;
(d) measuring the current flowing between the first electrode and the first electrically isolated test specimen; and
(e) repeating steps (a) through (d) for a second and third potential applied to the second electrode and to the second electrically isolated test specimen.

24. The method of claim 19 where the step of simultaneously measuring the atomic hydrogen permeation rate through the first electrically isolated test specimen and the corrosion rate of the second electrically isolated test specimen is performed first in the absence of an inhibitor designed to reduce either or both the hydrogen permeation rate and the corrosion rate, and then in the presence of such an inhibitor.

25. The method of claim 19 where the atomic hydrogen permeation rate is determined by measuring the pressure increase in a sealed chamber communicating with the surface of the first test specimen that is opposite the fluid reservoir.

26. A method for determining the permeation efficiency of a hydrogen induced cracking inhibitor in the presence of at least one compound which impedes the reaction of atomic hydrogen to molecular hydrogen, where permeation efficiency is a function of atomic hydrogen permeation current density and corrosion current density, comprising:

providing a reservoir of corrosive process solution;

simultaneously exposing a first electrically isolated test specimen and a first electrode, and a second electrically isolated test specimen and a second electrode to the process solution;

adding a first compound to said process solution reservoir to impede the reaction by which atomic hydrogen is converted to molecular hydrogen;

measuring the atomic hydrogen permeation current density of the first electrically isolated test specimen and the corrosion current density of the second electrically isolated test specimen in the presence of the first compound;

adding a second compound which inhibits hydrogen induced cracking;

measuring the atomic hydrogen permeation current density of the first electrically isolated test specimen and the corrosion current density of the second electrically isolated test specimen in the presence of the first and second compounds; and determining the permeation efficiency of the second compound, where permeation efficiency is defined as the ratio of the atomic hydrogen permeation current density to the corrosion current density.

27. The method of claim 26 where the process solution is brine.

28. The method of claim 26 where the first compound is hydrogen sulfide.

29. The method of claim 26 where the step of measuring the atomic hydrogen permeation current density of the first electrically isolated test specimen and the corrosion current density of the second electrically isolated test specimen comprises:

(a) applying a first voltage potential to the second electrode and to the second electrically isolated test specimen;

(b) measuring the current flow between the second electrode and the second electrically isolated test specimen at the first potential;

(c) simultaneously with steps (a) and (b), applying a voltage potential to the first electrode and to the first electrically isolated test specimen;

(d) measuring the current flow between the first electrode and the first electrically isolated test specimen; and (e) repeating steps (a) through (d) for a second and third voltage potential applied to the second electrode and to the second electrically isolated test specimen.

30. A method for evaluating compounds which inhibit hydrogen induced cracking of mild steel in the presence of hydrogen sulfide comprising:

(a) providing a reservoir containing process solution;

(b) simultaneously exposing a first electrically isolated test specimen and a second electrically isolated test specimen to said process solution in the presence of electrodes positioned in said reservoir;

(c) adding hydrogen sulfide to said process solution to impede the reaction of atomic hydrogen to molecular hydrogen;

(d) measuring the atomic hydrogen permeation rate through said first electrically isolated test specimen and the corrosion rate of said second electrically isolated test specimen in the presence of the hydrogen sulfide;

(e) adding a first inhibitor compound for inhibiting hydrogen induced corrosion;

(f) measuring the atomic hydrogen permeation rate through the first electrically isolated test specimen and the corrosion rate of the second electrically isolated test specimen in the presence of the first impeding and first inhibiting compounds;

(g) removing the process fluid, test samples and measurement electrodes from the test cell;

(h) repeating steps (a) through (g) for at least a second inhibiting compound; and (i) comparing measurement data obtained from steps (f) and (h) to determine the relative effectiveness of said first and at least second inhibiting compound for inhibiting hydrogen induced cracking.

31. The method of claim 30 where the process solution is brine.

32. The method of claim 30 where the atomic hydrogen permeation rate is characterized by atomic hydrogen permeation current density.

33. The method of claim 30 where the corrosion rate is characterized by corrosion current density.

34. The method of claim 30 where the relative effectiveness of two or more hydrogen induced cracking inhibitors is determined by:

(a) calculating the ratio of the atomic hydrogen permeation current density to the corrosion current density obtained in the presence of a first inhibitor;

(b) calculating said ratio for data obtained in the presence of a second inhibitor under the same conditions employed in step (a); and (c) making similar calculations for any additional inhibitors under the same conditions employed in step (a), where the inhibitor associated with the lowest value of the calculated ratios is ranked relatively more effective for inhibiting hydrogen induced cracking.

* * * * *